United States Patent
Zhou et al.

(10) Patent No.: US 11,013,487 B2
(45) Date of Patent: May 25, 2021

(54) METHOD AND APPARATUS FOR COMPUTED TOMOGRAPHY (CT) AND MATERIAL DECOMPOSITION WITH COUNT-RATE DEPENDENT PILEUP CORRECTION

(71) Applicant: CANON MEDICAL SYSTEMS CORPORATION, Otawara (JP)

(72) Inventors: Jian Zhou, Vernon Hills, IL (US); Xiaohui Zhan, Vernon Hills, IL (US); Zhou Yu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 15/929,155

(22) Filed: Oct. 18, 2019

(65) Prior Publication Data
US 2021/0113178 A1    Apr. 22, 2021

(51) Int. Cl.
*A61B 6/00* (2006.01)
*A61B 6/03* (2006.01)
*G01T 1/24* (2006.01)

(52) U.S. Cl.
CPC .............. *A61B 6/585* (2013.01); *A61B 6/032* (2013.01); *A61B 6/4241* (2013.01); *A61B 6/54* (2013.01); *A61B 6/4435* (2013.01); *G01T 1/24* (2013.01)

(58) Field of Classification Search
CPC ........... A61B 6/585; A61B 6/032; A61B 6/54; A61B 6/4241
See application file for complete search history.

(56) References Cited

U.S. PATENT DOCUMENTS

2014/0314211 A1* 10/2014 Zou .................. A61B 6/482
378/207
2016/0202364 A1    7/2016 Wang et al.
(Continued)

FOREIGN PATENT DOCUMENTS

WO    WO 2018/002226 A1    1/2018

OTHER PUBLICATIONS

J. Cammin, et al., "A cascaded model of spectral distortions due to spectral response effects and pulse pileup effects in a photon-counting x-ray detector for CT", Medical Physics, 2014.
(Continued)

*Primary Examiner* — Chih-Cheng Kao
(74) *Attorney, Agent, or Firm* — Oblon, McClelland, Maier & Neustadt, L.L.P.

(57) ABSTRACT

An apparatus and method are described using a forward model to correct pulse pileup in spectrally resolved X-ray projection data from photon-counting detectors (PCDs). The forward model represents pulse pileup effects using an integral in which the integrand includes a term that is a function of a count rate, which term is called a spectrum distortion correction function. This correction function can be represented as superposition of basis energy functions and corresponding polynomials of the count rate, which are defined by the polynomial coefficients. To calibrate the forward model, the polynomial coefficients are adjusted to optimize an objective function, which uses calibration data having known projections lengths for the material components of a material decomposition. To determine projection lengths for projection data from a computed tomography scan, the calibrated polynomial coefficients are held constant and the projection lengths are adjusted to optimize an objective function.

24 Claims, 8 Drawing Sheets

(56) References Cited

U.S. PATENT DOCUMENTS

2016/0287205 A1* 10/2016 Zou .................. A61B 6/4241
2017/0224299 A1* 8/2017 Petschke ............ A61B 6/032
2017/0231584 A1    8/2017 Konno
2018/0235562 A1* 8/2018 Petschke ............ A61B 6/032
2018/0329086 A1   11/2018 Roessl et al.

OTHER PUBLICATIONS

J. Dickmann, et al., "A count rate-dependent method for spectral distortion correction in photon counting CT", Mar. 9, 2018, SPIE, 2018.

B. Heismann, et al., Spectral Computed Tomography, Chapter 4: Techniques to Acquire Spectral CT Data, pp. 55-86, SPIE Press, 2014.

M. Kafaee, S. Saramad, "Pile-up correction by Genetic Algorithm and Artificial Neural Network", Nuclear Instruments and Methods in Physics Research A, vol. 607, pp. 652-658, 2009 (doi 10.1016/j.nima.2009.06.03).

K. Taguchi, et al., "Estimation of basis line-Integrals in a spectral distortion modeled photon counting detector using low-order polynomial approximation of X-ray transmittance", IEEE transaction on Medical Imaging, vol. 36 Issue 2, pp. 560-573, Oct. 26, 2016.

Z. Yu, et al., "Evaluation of conventional imaging performance in a research whole-body CT system with a photon-counting detector array", Phys Med Biol. 61 (4), pp. 1572-1595, Feb. 21, 2016.

\* cited by examiner

METHOD AND APPARATUS FOR COMPUTED TOMOGRAPHY (CT) AND MATERIAL DECOMPOSITION WITH COUNT-RATE DEPENDENT PILEUP CORRECTION

BACKGROUND

Field

Embodiments described herein relate generally to spectrally-resolved projection data in computed tomography (CT), and, more specifically, to correcting the projection data for pulse pileup arising in photon-counting detectors.

Description of the Related Art

Projection data can be used for many applications, including: computed tomography, radiography, mammography, and tomosynthesis. Projection data reveals the internal structure of an object by transmitting radiation through the object and detecting the effect of the object on the transmitted radiation by comparing transmitted radiation with the object present in the beam path versus when the object is absent. In absorption imaging the projection data represents Radon transforms of the attenuation along the rays traced by the radiation. Computed tomography (CT) uses projection data acquired for a series of projection angles to generate a sinogram from which an image of the internal structure of the object can be reconstructed. For example, a reconstruction algorithm, such as filtered back-projection or an iterative reconstruction method, can be used to approximate an inverse Radon transform to reconstruct a volumetric image from the series of projection images acquired at different projection angles.

CT imaging systems and methods are widely used for medical imaging and diagnosis. Typically an X-ray source is mounted on a gantry that revolves about a long axis of the body. An array of X-ray detector elements are mounted on the gantry, opposite the X-ray source. Cross-sectional images of the body are obtained by taking projective attenuation measurements at a series of gantry rotation angles, and processing the resultant projection data using a CT reconstruction algorithm.

Some CT scanners use energy-integrating detectors to measure CT projection data. Alternatively, photon-counting detectors (PCDs) have been developed using a semiconductor such as cadmium zinc telluride (CZT) capable of converting X-rays to photoelectrons to quickly and directly detect individual X-rays and their energies, which is advantageous for spectral CT. To obtain spectrally resolved projection data, the PCDs divide the X-ray beam into spectral bins (also called energy components) and count a number of photons in each of the bins, Many clinical applications can benefit from spectral CT technology, e.g., due to better material differentiation and improved beam hardening correction.

One advantage of spectral CT, and spectral X-ray imaging in general, is that materials having atoms with different atomic number Z also have different spectral profiles for attenuation. Thus, by measuring the attenuation at multiple X-ray energies, materials can be distinguished based on the spectral absorption profile of the constituent atoms (i.e., the effective Z of the material). Distinguishing materials in this manner enables a mapping from the spectral domain to the material domain, which is referred to as material decomposition.

Material decomposition of spectral CT data is possible because the attenuation of X-rays in biological materials is dominated by two physical processes—photoelectric and Compton scattering. Thus, the attenuation coefficient as a function of energy can be approximated by the decomposition $$\mu(E,x,y) = \mu_{PE}(E,x,y) + \mu_C(E,x,y)$$

wherein $\mu_{PE}(E, x, y)$ is the photoelectric attenuation and $\mu_C(E, x, y)$ is the Compton attenuation. This decomposition of the attenuation coefficient can be rearranged instead into a decomposition into two material components, with material 1 being a high-Z material such as bone and material 2 being a low-Z material such as water. Accordingly, the attenuation decomposition can be expressed as $$\mu(E,x,y) \approx \mu_1(E)c_1(x,y) + \mu_2(E)c_2(x,y),$$

wherein $c_{1,2}(x,y)$ is a spatial function describing the concentrations of material 1 and material 2 located at position $(x, y)$. The order of image reconstruction and material decomposition can be interchanged. When material decomposition is performed before image reconstruction, the spectral resolved attenuation at the pixels is resolved into projection lengths for the materials, such that the total attenuation at a photon-counting detector (PCD) due to the $i^{th}$ material components is the product of the projection length, $L_i$, and the attenuation coefficient of the $i^{th}$ material component, $\mu_i$, at a predefined density.

While semiconductor-based PCDs provide unique advantages for spectral CT, they also create unique challenges. For example, without correcting for nonlinearities and spectral shifts in the detector response, images reconstructed from semiconductor-based PCDs can have poorer image quality. The detector response corrections can include corrections for pileup, ballistic deficit effects, polar effects, characteristic X-ray escape, and space-charge effects. The combination of detector response correction and material decomposition creates a complex problem. Accordingly, computationally efficient methods are desired to correct for the spectral and nonlinear detector response of PCDs to ensure high-quality reconstructed images.

BRIEF DESCRIPTION OF THE DRAWINGS

A more complete understanding of this disclosure is provided by reference to the following detailed description when considered in connection with the accompanying drawings, wherein.

DETAILED DESCRIPTION

Photon-counting-detector based CT system (PCCT) have many advantages, including: spectrally resolving X-ray radiation, high-spatial resolution, and low electronic noise. At high X-ray flux rates, however, photon-counting detectors can suffer from pile up. That is, due to the count rate limitation of existing ASIC and semiconductor-detector technology, the measured count can deviate from the true count when the incident flux is sufficiently high that multiple X-ray photons are frequently incident on respective detector elements within the detection time window.

Figure 1A:
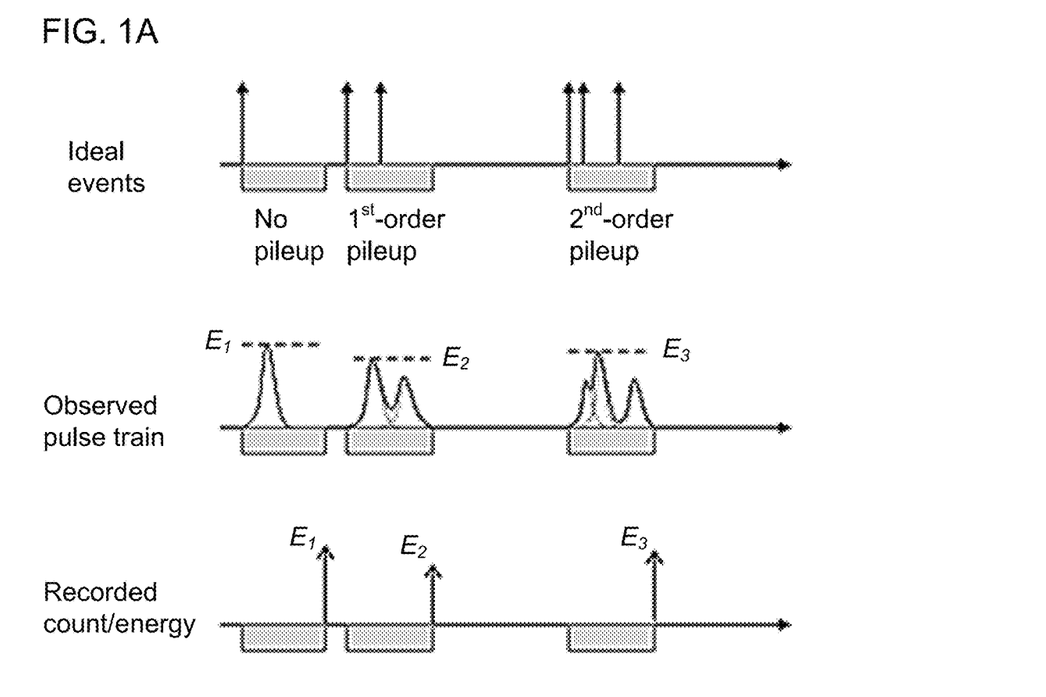
FIG. 1A shows examples of pulse trains illustrating no pileup, first-order pileup, and second-order pileup, and the signals generated for these pulse trains by an ideal detector (ideal events) and a non-ideal detector (observed pulse train), also shown are the recorded counts and energies for the non-ideal detector at the end of the respective detection windows, according to one implementation.
Figure 1B:
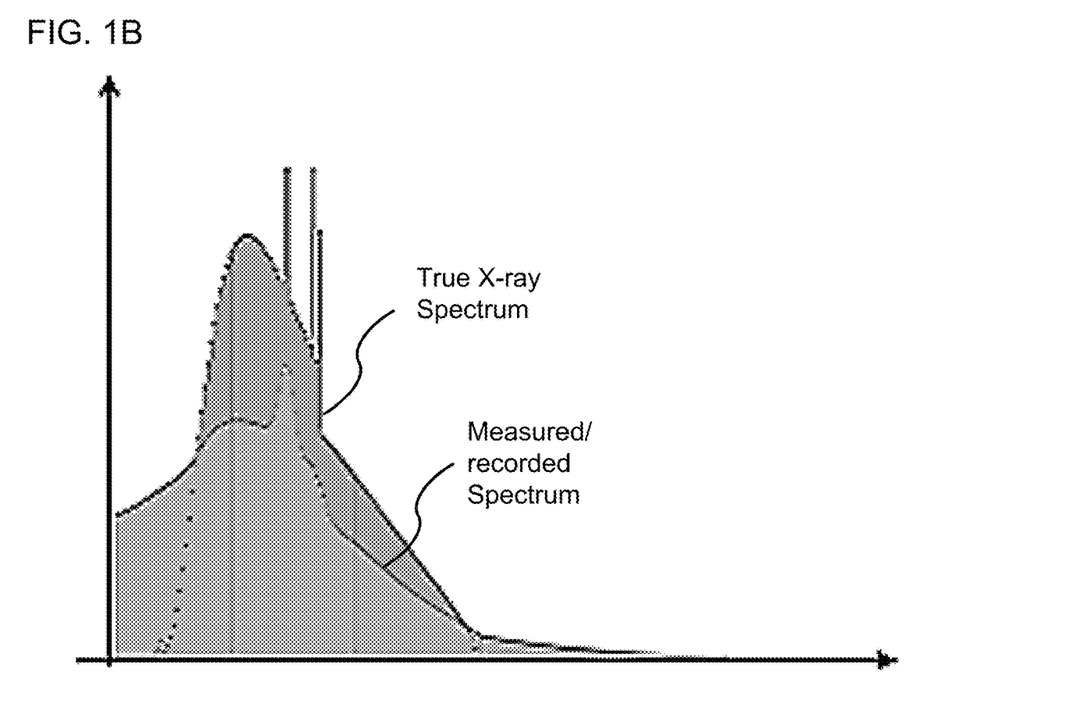
FIG. 1B shows a plot of an example of X-ray spectra for a true X-ray spectrum and a measured/recorded X-ray spectrum, illustrating a distortion due to pileup in non-ideal photon counting detectors, according to one implementation.

Referring now to the drawings, wherein like reference numerals designate identical or corresponding parts throughout the several views, the pileup effect is illustrated in FIGS. 1A and 1B, which show that in first-order and higher-order pile up the recorded/measured spectrum can become shifted relative to the actual spectrum of X-rays incident on the detector elements as a result of overlap and interactions between X-ray pulses/signals within given detector element during a detection time window. For example, in an ideal nonparalyzable (NP) detector ("ideal events" in FIG. 1A), the effects at high count rates due to multiple photons arriving during the detection window manifests as the multiple photons being counted as one X-ray photon having the highest energy detected during the detection window. Thus, even for this "ideal" case, the output count no longer accurately reflects the true counts, and the detected spectrum is distorted relative to the true spectrum. This effect is known as pulse pile up.

Moreover, for non-ideal detectors, physical effects due, e.g., to charge interactions between photo-electrons, depletion, saturation effects, etc. can cause further distortions of the measured spectrum relative to the true spectrum, as illustrated in the "observed pulse train" and "recorded count/energy" examples shown in FIG. 1A. Thus, the practical effect of pulse pile up is to shift of the recorded/measured energy spectrum relative to the true energy spectrum, as shown in FIG. 1B.

If left uncorrected, the detector response determines the distribution of actually energy deposited in photon counting detector, and an inaccurate response model will induce errors to the photon energy distributions, causing inaccurate decomposition results. Several strategies can counteract or otherwise minimize the effects of pileup. For example, making the area of detector elements smaller pushes the flux threshold higher before pileup becomes an issue, but the pileup effect still must be corrected for when this higher flux threshold is exceeded. When pixel size decreases and the flux rate per area is held constant, the count rate per pixel decreases proportionally to the decrease in detector area. Thus, small pixel design mitigates the pileup problem to a degree, but is not a complete solution. Moreover, decreasing the pixel size present other challenges, such as increasing charge sharing effects, which, like pile up, also causes spectral distortion and degrades the image quality and performance of the imaging system.

Additionally, an analytical model can be used to estimate and then correct for the pile-up effect. However, analytical models are limited by that fact that they are based on the analytical pulse shape an ideal NP detector, which is illustrated in FIG. 1A, and is not representative of the real detector response, leading to the model mismatch that could affect the accuracy of subsequent processing steps such as material decomposition and image reconstruction. Further, using analytical models for spectrum correction and then material decomposition would require the evaluation of a complete pileup response function, which is resource intensive both in terms of storage and computation. For example, precomputing and storing an analytical model would demand a lot of storage space and hence would not be practical, in particular, when the full pileup response function varies from element-to-element of the detector array. Alternatively, calculating the pileup response function on-the-fly is also not currently practical because of the length of time these computations would require.

Using heuristic models such as a neural network to correct for the detector response also have their drawbacks. For example, these methods require a large set of training data to estimate the model parameters. But even with a large set of training data, the training does not guarantee a global minimizer because the objective function used for training is nonconvex, posing an obstacle to maintaining stability and robustness when correcting for pileup using a neural network. Also, the use the neural network method for the pileup correction with realistic detector is an under-developed field that remains poorly understood.

The above challenges result from the combining non-ideal detectors with the effects of pileup. To address these challenges, the methods described herein use a generalized forward model that includes a count rate dependent term $Q_b(U, c_t)$ to model the pulse pile effects (PPE)

$$y_b = \int_0^{U_{max}} Q_b(U, c_t) dU \left( \int_0^{E_{max}} R(U, E) \Phi_0(E) \exp\left(-\sum_{m=1}^{M} \mu_m(E) l_m\right) dE \right),$$

wherein $y_b$ is the number of gamma rays detected in the $b^{th}$ energy bin, $Q_b(U, c_t)$ is the generalized spectrum distortion correction function, which is a function of energy U and count rate $c_t$, $R(U, E)$ is a linear detector response function, $\Phi_0(E)$ is an input spectrum, which can include the effect of detector efficiency, $\mu_m(E)$ is the linear attenuation coefficients for the $m^{th}$ basis material. The count rate $c_t$ can be a measured bin count rate, a total count rate (e.g., by summing the bin count rates, or another value that is derived from the count rate, a function of the count rate, or any value that is otherwise related to the count rate.

Figure 2:
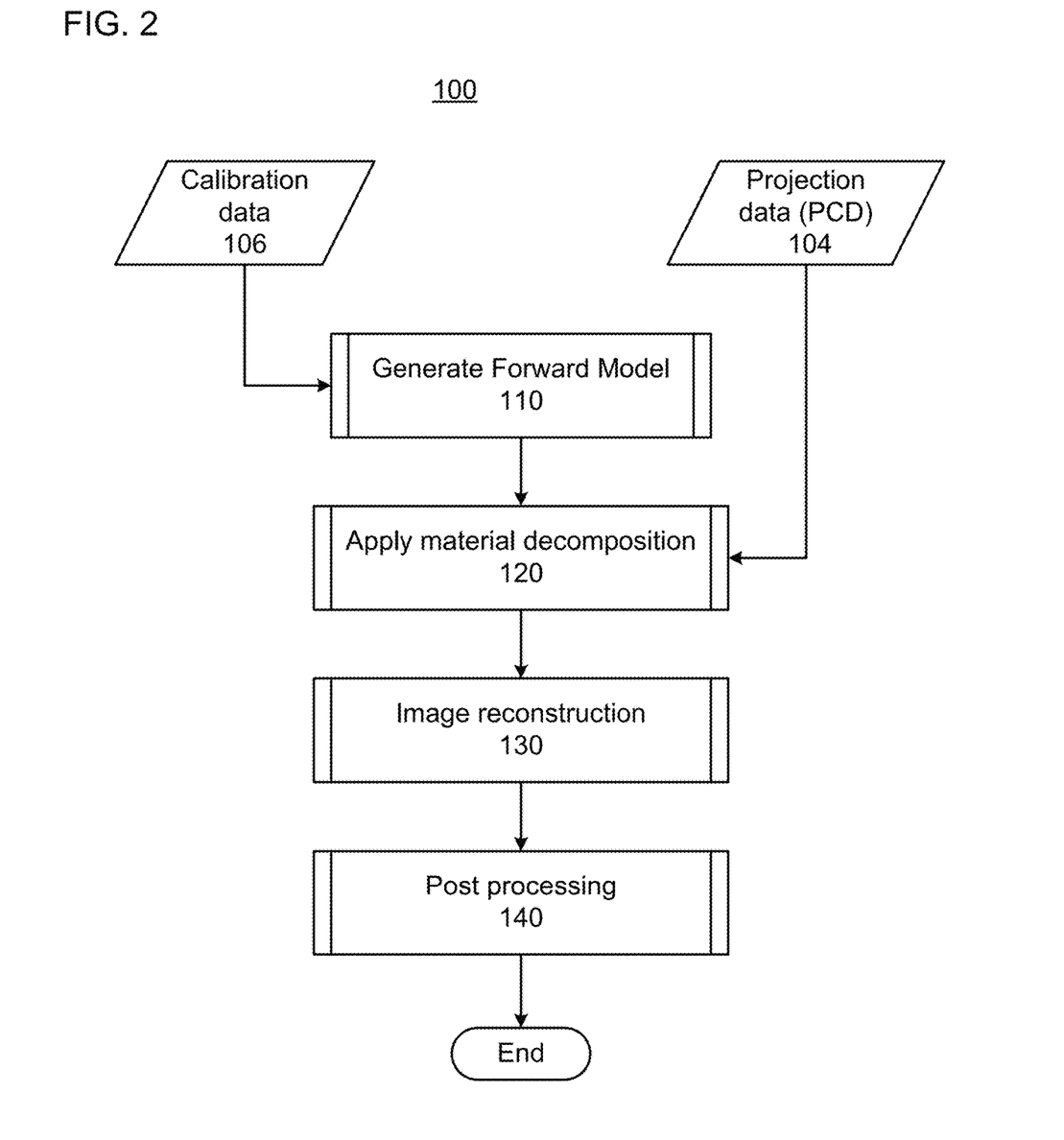
FIG. 2 shows a flow diagram of a method to correct projection data using a forward model of pileup, and then reconstruct a computed tomography (CT) image using projection lengths derived using the forward model, according to one implementation.

The methods described herein can be better appreciated by considering the non-limiting flow diagram of method 100, shown in FIG. 2. The flow diagram of method 100 represents an overall workflow for a PCCT pileup correction, material decomposition, and image reconstruction. The above discussed improvements and advantages of the methods described herein are variously included in implementations of processes 110 and 120, which are directed to generating a forward model representing the real pileup effect and detector response measured in the calibration data 106 to correct for pileup; and performing a material decomposition. That is, in spectral CT using photon-counting detectors (PCDs), an image reconstruction process 130 is preceded by preprocessing steps including correcting for the detector response and material decomposition.

FIG. 2 shows a flow diagram of method 100 for reconstructing an image of an object OBJ based on a series of projection measurements of the object OBJ performed at different projection directions (i.e., computed tomography (CT) using projective measurements). The data processing is performed using two inputs—calibration values 106 and projection data 104. The projection data have multiple spectral components, making it compatible with material decomposition based on the different spectral absorption characteristics of high-Z and low-Z materials. In addition to being applicable to CT applications as illustrated by the non-limiting example in FIG. 2, processes 110 and 120 are also applicable to non-CT applications involving projective measurements, including radiography, mammography, and tomosynthesis, which are within the scope of the apparatuses and methods described herein and do not depart from the spirit of this disclosure, as would be appreciated by a person of ordinary skill in the art.

Process 110 of the image reconstruction method 100 corrects the projection data for the real detector response, including pileup. This can include using various calibrations 106 to precompute a feed forward model.

Next, the method 100 proceeds to process 120, in which the spectrally resolved projection data is corrected to account for pulse pileup using the feed forward model, and various other calibrations can be applied to correct the projection data (e.g., denoising, background subtraction, corrections for nonlinear-detector response, etc.). The corrections can be applied prior to, after, or in conjunction with the decomposition of the spectral components into material components, while still in the projection domain (i.e., before image reconstruction).

Although images of the object OBJ can be reconstructed from the spectral components of the projection data and then material decomposition is performed in the image domain on these spectral-component images without departing from the spirit of the disclosure, this alternative order of the processing steps will not be described in the non-limiting example illustrated in FIG. 2.

After process 120, the method 100 proceeds to process 130, in which multiple images are reconstructed using an image reconstruction process (e.g., an inverse Radon transformation). The image reconstruction can be performed using a back-projection method, a filtered back-projection, a Fourier-transform-based image reconstruction method, an iterative image reconstruction method (e.g., algebraic reconstruction technique or the like), a matrix-inversion image reconstruction method, or a statistical image reconstruction method. For non-CT applications (e.g., radiography, mammography, and tomosynthesis), process 130 is omitted, and the non-CT application can proceed directly from process 120 to either process 140 or process 150.

After process 130, the method 100 proceeds to process 140 wherein post-processing steps are performed on the data, including: volume rendering, smoothing, denoising, filtering, and various methods for combining the material images to convey physical concept (e.g., maps of the attenuation, density, or effective Z density).

Example denoising methods include linear smoothing filters, anisotropic diffusion, non-local means, or nonlinear filters. Linear smoothing filters remove noise by convolving the original image with a convolution kernel that represents a low-pass filter or smoothing operation. For example, a Gaussian convolution kernel comprises elements determined by a Gaussian function. This convolution brings the value of each pixel into closer agreement with the values of its neighbors. Anisotropic diffusion removes noise while preserving sharp edges by evolving an image under a smoothing partial differential equation similar to the heat equation. A median filter is an example of a nonlinear filter and, if properly designed, a nonlinear filter can also preserve edges and avoid blurring. The median filter is one example of a rank-conditioned rank-selection (RCRS) filter, which can be applied to remove salt and pepper noise from an image without introducing significant blurring artifacts. Additionally, a filter using a total-variation (TV) minimization regularization term can be applied if imaged region supports an assumption of uniformity over large areas that are demarked by sharp boundaries between the uniform areas. A TV filter is another example of a nonlinear filter. Moreover, non-local means filtering is an exemplary method of determining denoised pixels using a weighted average over similar patches within the images.

Finally, in step 150 of method 100 the image is presented to a user. The image presentation can be performed by displaying the image on a digital screen (e.g., LCD monitor), by printing the image on a suitable medium (e.g., paper or an X-ray film), or by storing the image on a computer-readable medium.

The discussion herein is focused primarily on process 110 and process 120. As discussed above, these processes are applicable to both CT and non-CT applications, including: radiography, mammography, and tomosynthesis, which are within the applications of the methods described herein, as would be understood by a person of ordinary skill in the art.

In summary, according to a non-limiting implementation, method 100 includes, at process 110, generating a lower dimension pulse pileup model/parameters in forward model, which is precomputed from calibration data 106 with real detector response and the stored in a non-transitory computer readable medium of a CT apparatus. Further, method 100 includes, at process 120, applying material decomposition, either after or together with the application of the precomputed pileup model, to projection data 104 from photon-counting detectors (PCDs) to compute the path length of different material from real PCCT measurements. At process 130, method 100 includes reconstructing material images from the material-component path lengths generated at process 120. The reconstruction method used in process 130 can be any known method, including analytical reconstruction methods and iteration reconstruction methods. At process 140, method 100 includes post-processing such as artifact reduction techniques that are applied to further improve image quality.

The discussion below focuses primarily on process 110 and process 120. As discussed above, these processes are applicable to both CT and non-CT applications, including: radiography, mammography, and tomosynthesis, which are within the spirit of the disclosure, as would be understood by a person of ordinary skill in the art.

Returning to process 110, the projection data correction can be represented by the recorded/measured energy $S_{out}(U)$ derived from the energy spectrum of X-rays incident on the detector $S_{in}(U)$, wherein an implementation of the detector response function is given by $$S_{out}(U) = ne^{-n\tau} \int dE R_0(U,E)\Phi_0(E) +$$
$$n^2 e^{-n\tau} \int\int dE dE' R_1(U,E,E')\Phi_0(E)\Phi_0(E') + \text{higher order}$$

wherein $R_0$ is the linear response function, $R_1$ is the quadratic response function representing first-order pileup, and $\tau$ is the dead time of the detector. The measured energy spectrum $S_{out}(E)$ also depends on higher-order terms, including second-order pileup, etc. The input spectrum is $$\Phi_0(E) = g(E) \times S_{in}(E),$$

wherein $g(E)$ can be 1 in certain implementations and in other implementations $g(E)$ can be a function accounting for detector efficiency/loss (e.g., representing energy dependence of the quantum efficiency of the detectors and loss due to Fresnel reflection at the air-detector boundary). The incident spectrum $S_{in}(E)$ is given by $$S_{in}(E) = S_{air}(E) \prod_{m=1}^{M} \exp(-\mu_m(E) l_m),$$

wherein $\mu_m$ is the attenuation coefficient of the $m^{th}$ basis material of a material decomposition, $l_m$ is a projection length of the $m^{th}$ basis material, and $S_{air}$ is the X-ray radiation incident on the detector in the absence of an attenuating object OBJ (i.e., =0 for all m).

The number of counts in the $b^{th}$ energy bin can be $$N_b = \Delta T \int dE w_b(E) S_{out}(E),$$

wherein $\Delta T$ is the integration time and $w_b(E)$ is the spectral function of the $b^{th}$ energy bin of the photon counting detectors. For example, the spectral function could be a square function (i.e., a zero-order spline function), which is defined as $$w_b(E) = \begin{cases} 1 & W_b < E < W_{b+1} \\ 0 & \text{otherwise} \end{cases}.$$

The methods described herein use a general forward model to approximate the counts at the $b^{th}$ energy bin by the value $y_b$, which is given by $$y_b = \int_0^{U_{max}} Q_b(U, c_t) dU \int_0^{E_{max}} R(U,E)\Phi_0(E) \exp\left(-\sum_{m=1}^{M} \mu_m(E) l_m\right) dE.$$

wherein $y_b$ is the number of gamma rays detected in the $b^{th}$ energy bin, $Q_b(U, c_t)$ is the generalized spectrum distortion correction function, which is a function of energy U and count rate $c_t$, $R(U,E)$ is a, linear detector response function, $\Phi_0(E)$ is an input spectrum, which can include the effect of detector efficiency, $\mu_m(E)$ is the linear attenuation coefficients for the $m^{th}$ basis material. The forward model to calculate $y_b$ can be better understood by considering the integrand of the inner integral (i.e., the integral over the energy variable E) models linear spectral response effects (SRE), such as k-escape, whereas the integrand in the outer integral (i.e., the integral over the energy variable U) models pulse pileup effects (PPE) and other nonlinear detector responses. Thus, the forward model is consistent with a cascaded process in which the linear SRE are modelled first, and the results of the SRE model are applied as an input to then model the non-linear PPE.

Figure 3A:
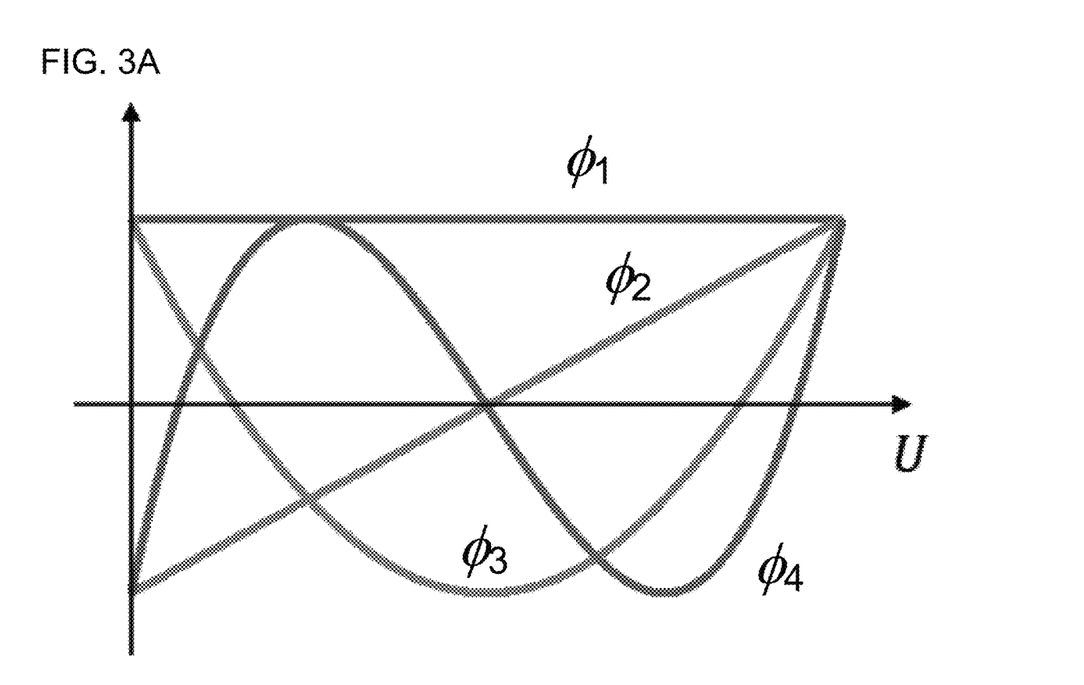
FIG. 3A shows a plot of polynomials being used as basis energy functions, according to one implementation.
Figure 3B:
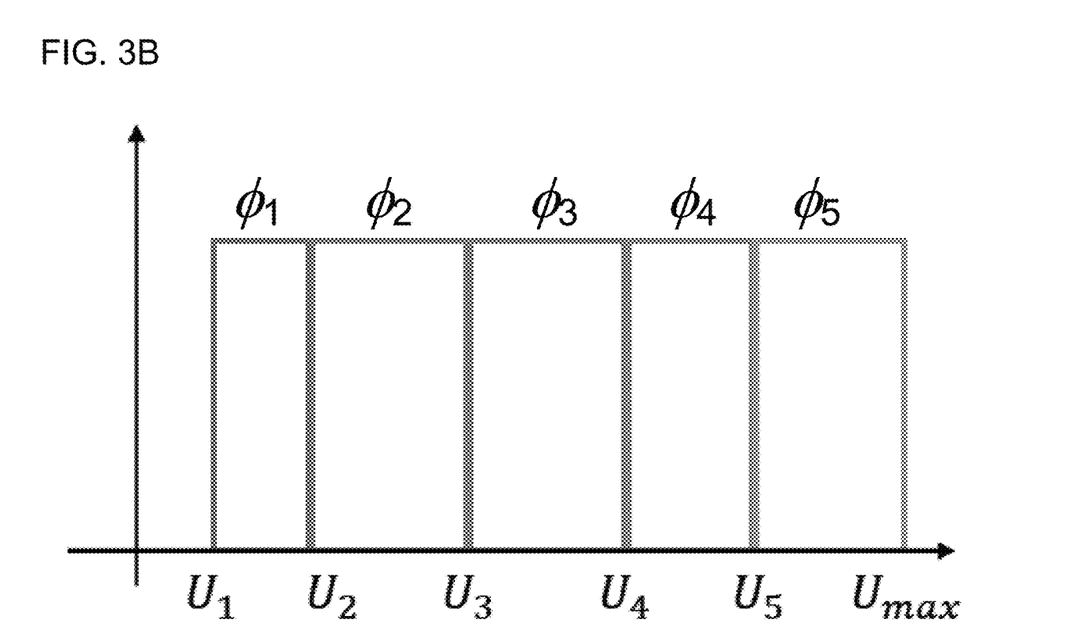
FIG. 3B shows a plot of zero-order splines being used as the basis energy functions, according to one implementation.

Calibration data can be used to learn the coefficients in the count-dependent correction term $Q_b$ (also referred to as the "generalized spectrum distortion correction function") that best corrects for the nonlinear by the respective PCDs. For example, the pulse pile effects (PPE) count-dependent correction term $Q_b$ can be a linear combination of basis functions. In certain implementations, the count-dependent correction term $Q_b$ can take the form, but is not limited to, $$Q_b(U, c_t) = \sum_{i=1} f_i(c_b | \theta_{bi}) \phi_i(U)$$

wherein $f_i(c_t|\theta_{bi})$ is the $i^{th}$ count rate function of energy bin b in which $\theta_{bi}$ are learned coefficients and $c_t$ is the input variable; and $\phi_i(U)$ is the $i^{th}$ basis energy function for bin b. The function $f_i(c_t|\theta_{bi})$ can also be referred to as a parameterized function of the count rate, in which $\theta_{bi}$ are the parameters. The coefficient vector $\theta_{bi}$ is an array of values (e.g., $\theta_{bi} = \{a_{bi,0}, a_{bi,1}, a_{bi,2}\}$) to be learned from the calibration training data, as described in more detail below. In one non-limiting implementations, $f_i(c_t|\theta_{bi})$ can be a polynomial function of the count rate:

$$f_i(c_t|\theta_{bi}) = a_{bi,0} + a_{bi,1} c_t + a_{bi,2} c_t^2$$

wherein $\theta_{bi} = \{a_{bi,0}, a_{bi,1}, a_{bi,2}\}$,

FIGS. 3A and 3B show two examples of basis-energy functions $\phi_i(U)$. In FIG. 3A the basis-energy functions $\phi_i(U)$ are polynomials. For example, the can be $\phi_i(U)$ Laguerre polynomials over the domain spanning the energy bins (i.e., $U \in [U_1, U_{max}]$). In another implementation, basis-energy functions $\phi_i(U)$ can be zero-order spline functions, as shown in FIG. 3B. Here, the basis energy function for bin i can be given as $$\phi_i(U) = \begin{cases} 1 & \text{if } U \in [U_i, U_{i+1}) \\ 0 & \text{otherwise} \end{cases}.$$

To determine the coefficients $\theta_{bi}$, calibration data 106 is obtained for which the projection lengths are known. For example, the calibration data 106 can be acquired using phantoms of known size, shape, and material types. Given the known projection lengths $\hat{l}_m(n)$, the model coefficients $\theta_{bi}$ can be estimated as by minimizing the following weighed least square function $$L(\theta_{bi}) = \sum_n \sum_b \left\{ w_b^{(n)} (N_b^{(n)} - y_b^{(n)}(\theta_{bi}))^2 \right\},$$

wherein $N_b^{(n)}$ is the number of count of the $b^{th}$ energy bin of the $n^{th}$ calibration data, and $$y_b^{(n)}(\theta_{bi}) = \sum_i f_i(c_r^{(n)} | \theta_{bi}) \int \int dEdU \phi_i(U) R(U, E) dU \Phi_0^{(n)}(E) \exp\left(-\sum_m \mu_m(E) \hat{l}_m^{(n)}\right),$$

wherein the subscripts and superscripts n indicates the $n^{th}$ calibration data. For example, $c_t^{(n)}$ is the count rate of the $n^{th}$ calibration data, and $w_b^{(n)}$ is a weight for the $b^{th}$ energy bin of the $n^{th}$ calibration data (e.g., the weight can be based on the signal-t-noise ratio (SNR) or some other indicia of the quality/reliability of the $n^{th}$ calibration data). The $n^{th}$ calibration data can be an $n^{th}$ CT scan or projection measurement performed using an $n^{th}$ phantom. Using the weighed least square function $L(\theta_{bi})$, the model coefficients $\theta_{bi}$ can be estimated by solving the optimization problem $$\hat{\theta}_{bi} = \underset{\theta_{bi}}{\operatorname{argmin}}\{L(\theta_{bi})\}.$$

In step 120, the model coefficients $\hat{\theta}_{bi}$ are fixed and the optimization problem is to solve for the projection lengths $l_m$ that minimize the weighted least square function, where the subscription real indicates a real measurement $$L(l) = \sum_b w_b^{(s)}\left(N_b^{(s)} - y_b(l | \hat{\theta}_{bi})\right)^2,$$

wherein the superscripts s indicate values generated during a scan to acquire the projection data 104, $N_b^{(s)}$ is the number of X-rays detected in the $b^{th}$ energy bin of a given pixel of the projection data, $l=\{l_1, \ldots l_M\}$ is a vector of all of the projection lengths for the given pixel in the projection data, and the number of X-rays $y_b(l|\hat{\theta}_{bi})$ that are calculated using the forward model is given by $$y_b(l | \hat{\theta}_{bi}) = \sum_i f_i(c_b^{(s)} | \hat{\theta}_{bi}) \int \int \phi_i(U) R(U, E) dU \Phi_0^{(s)}(E) \exp\left(-\sum_m \mu_m(E) l_m\right) dEdU,$$

wherein $c_b^{(s)}$ is the count rate (which can be independent of the given pixel), and $\Phi_0^{(s)}(E)$ is the energy spectrum during the scan corresponding to the given pixel in the absence of the imaged object (OBJ). The projection lengths $l=\{l_1, \ldots l_M\}$ can be found by solving the optimization problem $$\hat{l} = \underset{l}{\operatorname{argmin}} L(l) \text{ s.t. } l_m \geq 0 \text{ for all } m.$$

In general, any known method can be used to iteratively converge to the argument optimizing the objective function. For example, objective function can be optimized using an optimization search such as a steepest descent method, a gradient-based method, a genetic algorithm, a simulated annealing method, or other known method of searching for an argument that optimizes the objective function. Further, the argument used in the optimization search can be the spectrally resolved count rates or the projection lengths of material components.

The examples above use as a weighted least square function for the objective functions, but the methods described herein can be implemented using other functional forms for the objection functions. For example, determining the optimal projection lengths $l=\{l_1, \ldots l_M\}$ can be performed by optimizing the objective functions L(l) described below.

In one implementation, the objective function is the least squares of the difference between the measured counts $N_b^{(s)}$ and the calculated counts from the forward model $y_b(l|\hat{\theta}_{bi})$, i.e., $$L(l) = \sum_m \left(N_b^{(s)} - y_b(l | \hat{\theta}_{bi})\right)^2.$$

In one implementation, the objective function is the weighted least squares of the difference between the measured counts $N_b^{(s)}$ and the calculated counts from the forward model $y_b(l|\hat{\theta}_{bi})$, i.e., $$L(l) = \sum_m \frac{\left(N_b^{(s)} - y_b(l | \hat{\theta}_{bi})\right)^2}{\sigma_m^2},$$

where $\sigma_m$ is a measure of the measurement uncertainty of the $m^{th}$ energy bin of detector.

In one implementation, the objective function is the Poisson likelihood function, i.e., $$L(l) = \sum_m \left[N_b^{(s)} \log(y_b(l | \hat{\theta}_{bi})) - y_b(l | \hat{\theta}_{bi})\right].$$

Figure 4:
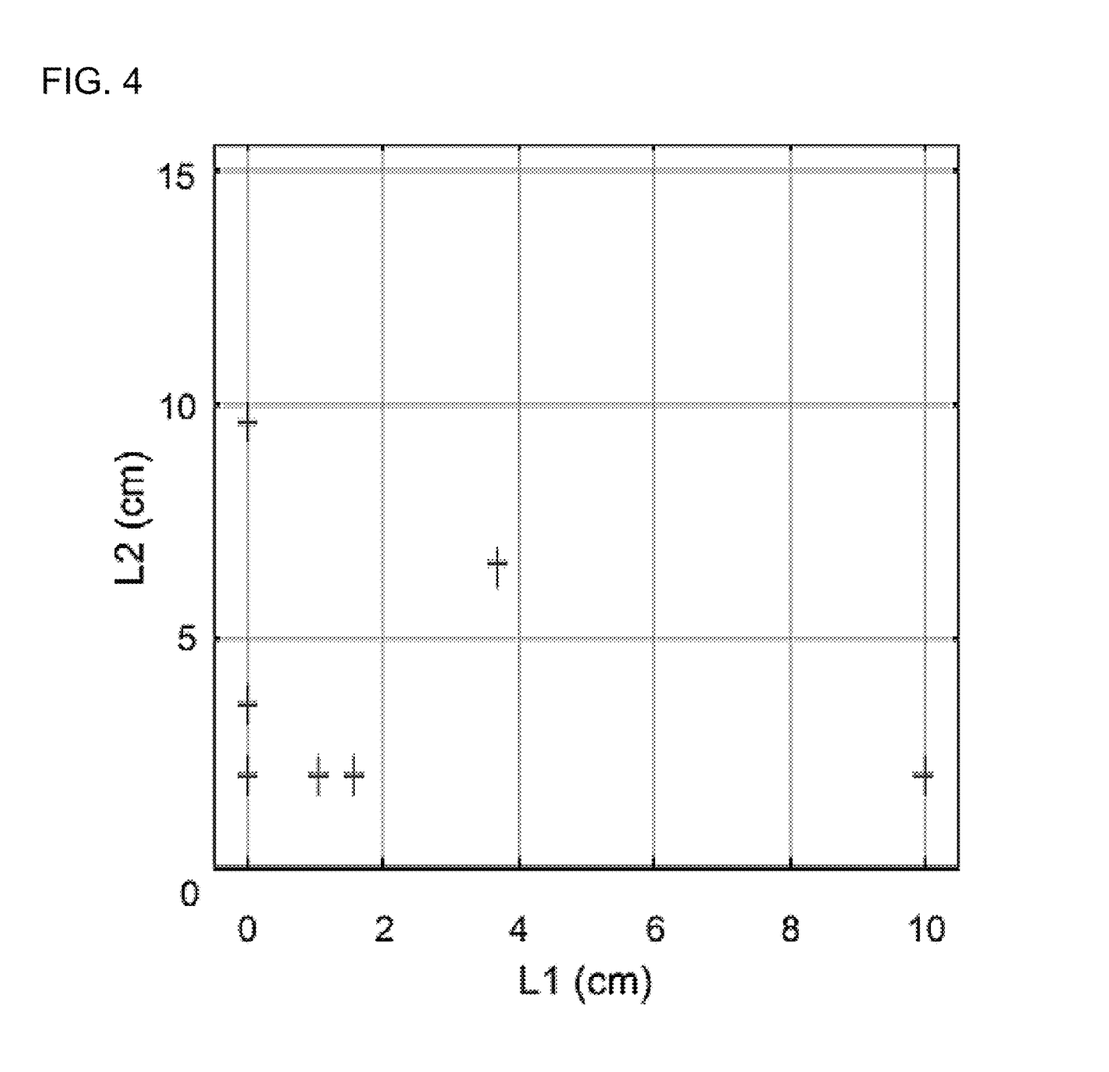
FIG. 4 shows projection lengths used to calibrate the forward model, according to one implementation.

FIG. 4 shows a plot of seven combinations of projection lengths $l_1$ and $l_2$ that were used determine 60 parameters (i.e., $\hat{\theta}_{bi} = \{a_{bi,0}, a_{bi,1}, a_{bi,2}\}$, wherein b={1, . . . 5} and i={1, . . . 4}). The calibration data includes measurements for these seven combinations of projection lengths, which are acquired using four different current settings for the X-ray tube (i.e., 200, 400, 600, and 800 mA), resulting in a 140 measurements to solve for 60 parameters $\hat{\theta}_{bi}$ (i.e., five energy bins times seven combinations of the projection lengths times four current settings results in 5×7×4=140). These 140 measurements in the calibration data are sufficient to generate a good model, as is evidenced by comparing FIGS. 5 and 6A.

Figure 5:
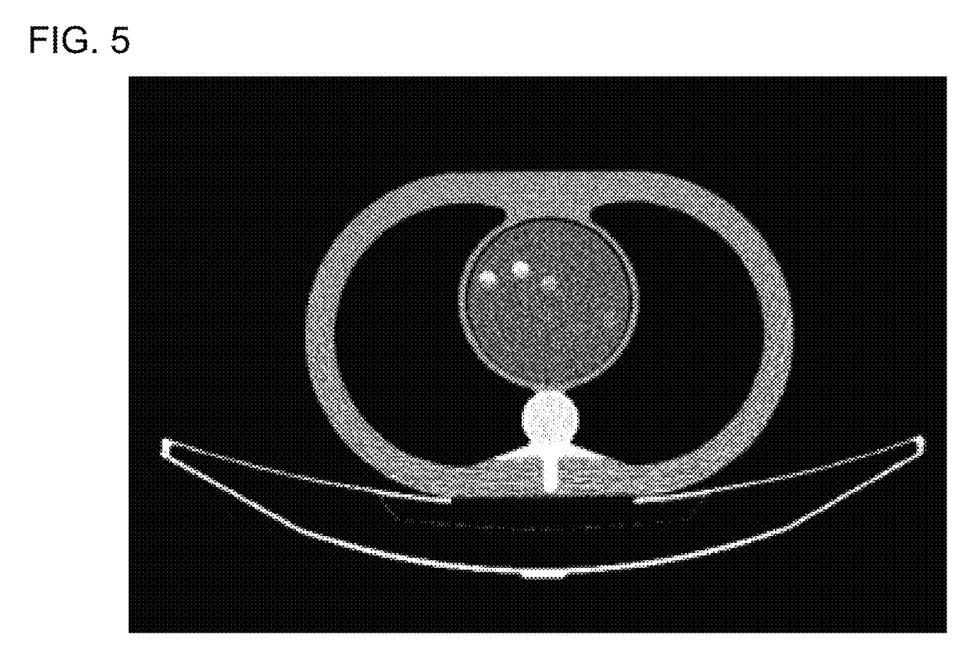
FIG. 5 shows a reference CT image of a phantom, according to one implementation.
Figure 6A:
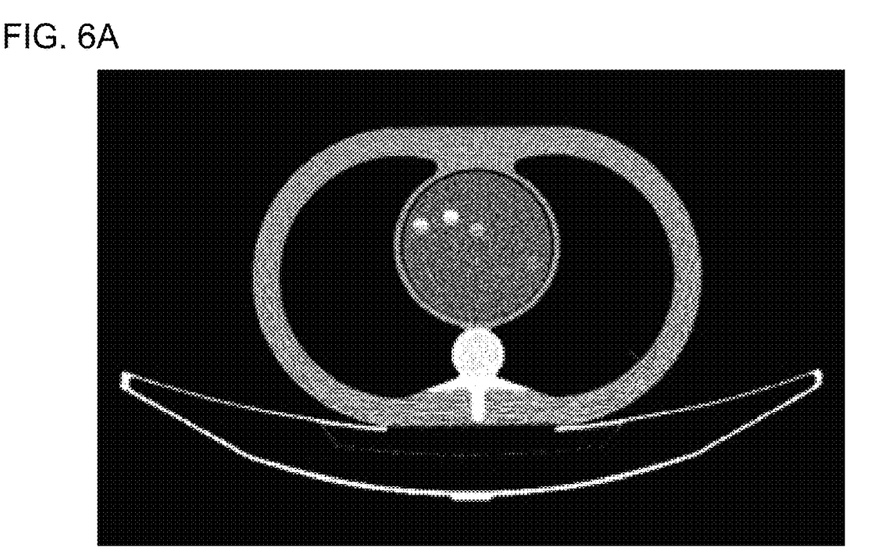
FIG. 6A shows a CT image of the phantom that has been reconstructed using the forward model together with the method described herein, according to one implementation.
Figure 6B:
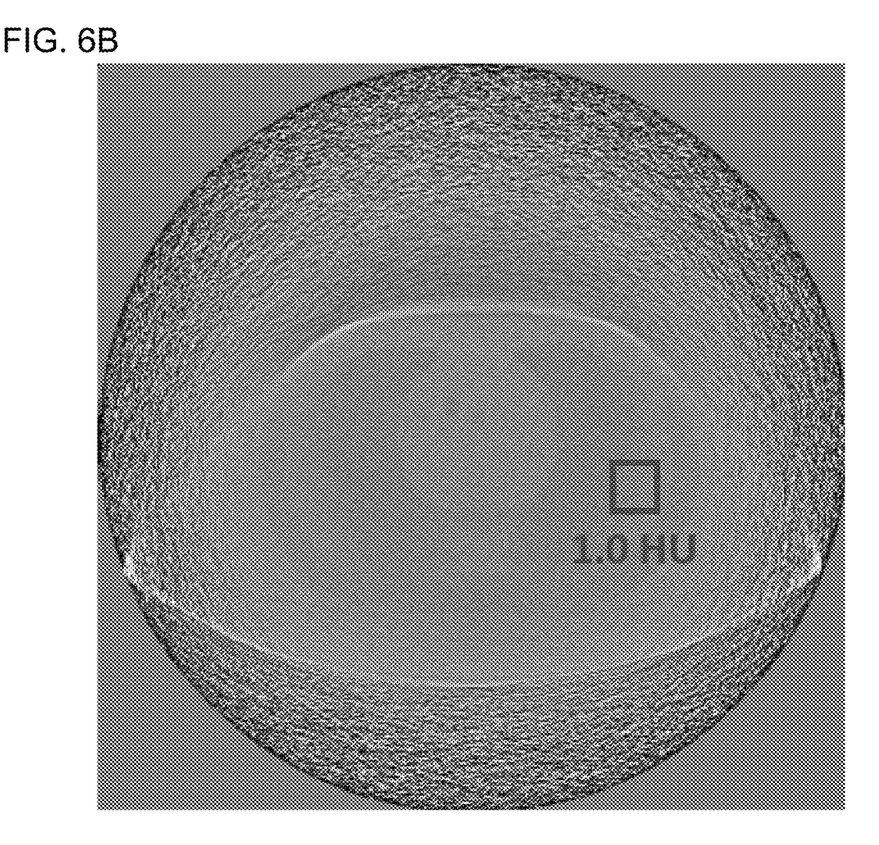
FIG. 6B shows a difference image for a difference between the reference image of FIG. 5 and the CT image of FIG. 6A, according to one implementation.

FIG. 5 shows a reference image for a CT image (i.e., a gold standard to which the method described herein can be compared). FIG. 6A shows a CT image that was reconstructed using the forward model described herein. FIG. 6B shows a difference image obtained by subtracting the CT image in FIG. 6A from the CT image in FIG. 5. In the square region that has been superimposed on the difference image in FIG. 6B the average values in 1.0 Hounsfield Units (HU). This can be compared with a related method for correcting detector nonlinearities, which is described in J. Dickmann, et al, "A count rate-dependent method for spectral distortion correction in photon counting CT," Proc. SPIE 10573, Medical Imaging 2018: Physics of Medical Imaging, 1057311 (9 Mar. 2018).

Figure 7A:
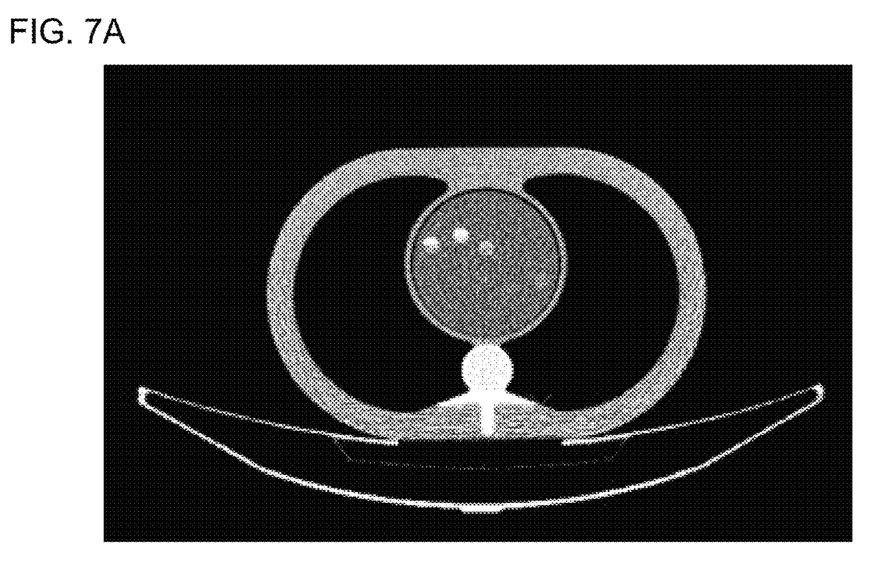
FIG. 7A shows a CT image of the phantom that has been reconstructed using using a related pileup correction method, according to one implementation.
Figure 7B:
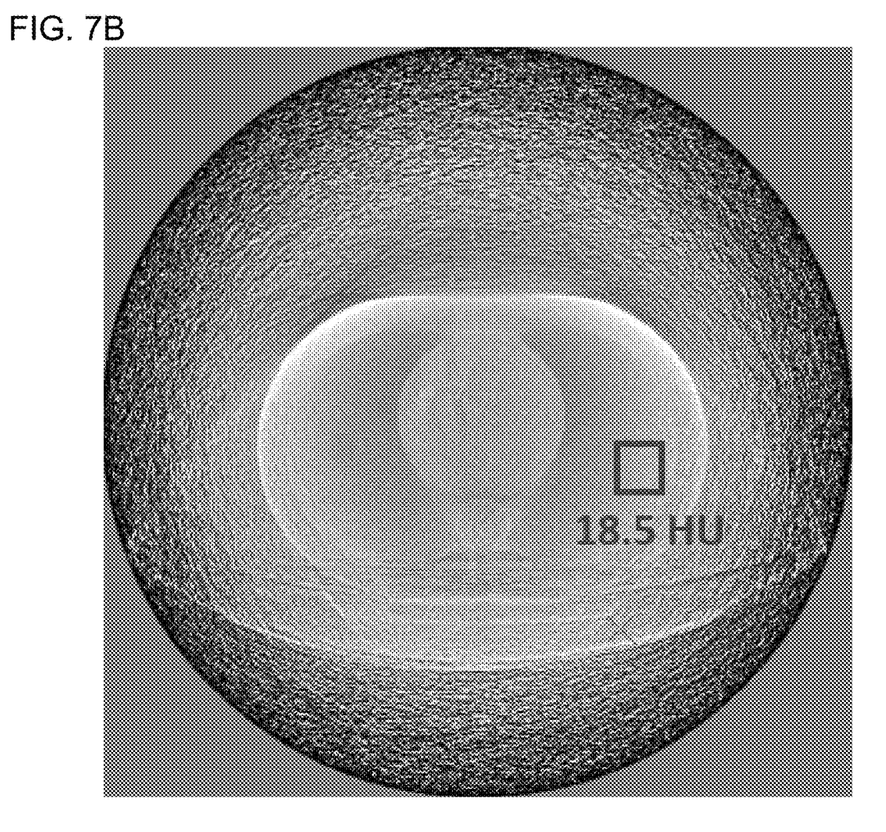
FIG. 7B shows a difference image for a difference between the reference image of FIG. 5 and the CT image of FIG. 7A, according to one implementation.

FIG. 7A shows a CT image that was reconstructed using the related method noted above. FIG. 7B shows a difference image obtained by subtracting the CT image in FIG. 7A from the CT image in FIG. 5. In the square region that has been superimposed on the difference image in FIG. 7B the average values in 18.5 HU. Accordingly, using the forward model described herein can provide an order of magnitude improvement over the related method noted above.

Figure 8:
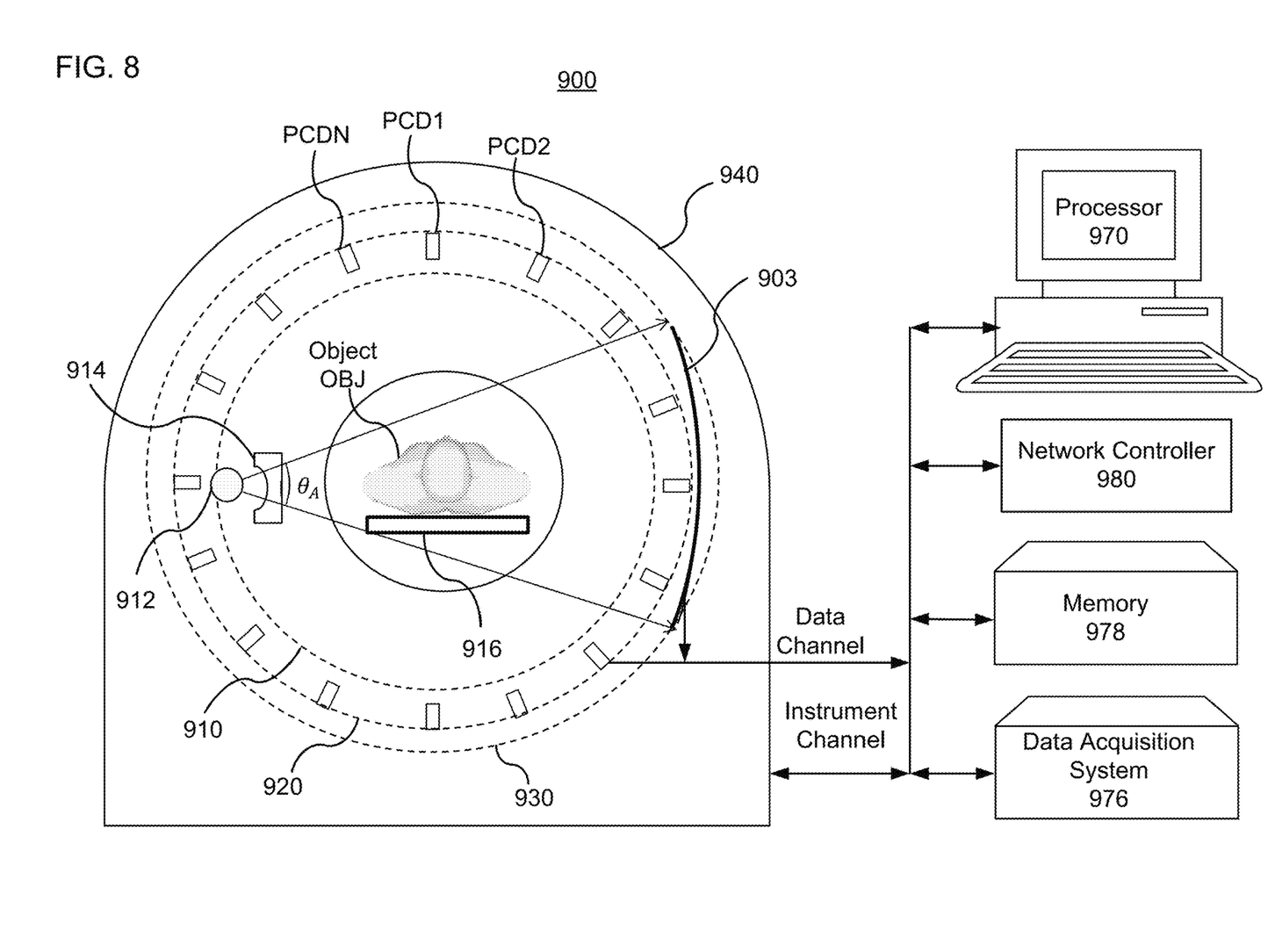
FIG. 8 shows a schematic of an implementation of a CT scanner, according to one implementation.

FIG. 8 shows a computed tomography (CT) scanner 900 having both energy-integrating detectors arranged in a third-generation geometry and PCDs arranged in a fourth-generation geometry. Illustrated in FIG. 8 is an implementation for placing the PCDs in a predetermined fourth-generation geometry in combination with a detector unit 903 in a predetermined third-generation geometry in a CT scanner system. The diagram illustrates relative positions among the X-ray source 912, the collimator/filter 914, the X-ray detector 903, and the photon-counting detectors PCD1 through PCDN. The projection data 104 can be obtained using the CT scanner 900, and the projection data 104 can be obtained using the CT scanner 900 in which the detector unit 903 is omitted.

In addition to the configuration of the X-ray source 912 and the detectors including the detector unit 903 and the PCDS show in FIG. 8, other types and combinations of X-ray detectors and X-ray source can be used to obtain the projection data. For example, either the detector unit 903 or the PCDS could be omitted from the scanner shown in FIG. 8 and the scanner could still obtain projection data, albeit different from the projection data obtained using the complete system shown in FIG. 8. In certain implementations, the PCDS can be direct X-ray detectors using semiconductors to convert the X-rays directly to photoelectrons without first generating scintillation photons. Additionally, in certain implementations, a broadband X-ray source can be used with spectrally-resolving X-ray detectors. These spectrally-resolving X-ray detectors can include PCDs in any configurations (e.g., a predetermined third-generation geometry or a predetermined fourth-generation geometry) or energy-integrating detectors preceded by respective spectral filters. In certain implementations, the X-ray source can include multiple narrow-band X-ray sources, such as in a dual source CT scanner. In general, any known combination of detector type and configuration together with any known type or combination of X-ray sources can be used to generate the projection data.

Returning to FIG. 8, circuitry and hardware are also shown for acquiring, storing, processing, and distributing X-ray projection data. The circuitry and hardware include: a processor 970, a network controller 980, a memory 978, and a data acquisition system 976.

In one alternative implementation, the CT scanner includes PCDs but does not include the energy-integrating detector unit 903.

As the X-ray source 912 and the detector unit 903 are housed in a gantry 940 and rotate around circular paths 910 and 930 respectively, the photon-counting detectors PCDs and the detector unit 903 respectively detects the transmitted X-ray radiation during data acquisition. The photon-counting detectors PCD1 through PCDN intermittently detect the X-ray radiation that has been transmitted and individually output a count value representing a number of photons, for each of the predetermined energy bins. On the other hand, the detector elements in the detector unit 903 continuously detect the X-ray radiation that has been transmitted and output the detected signals as the detector unit 903 rotates. In one implementation, the detector unit 903 has densely placed energy-integrating detectors in predetermined channel and segment directions on the detector unit surface.

In one implementation, the X-ray source 912, the PCDs and the detector unit 903 collectively form three predetermined circular paths that differ in radius. At least one X-ray source 912 rotates along a first circular path 910 while the photon-counting detectors are sparsely placed along a second circular path 920. Further, the detector unit 903 travels along a third circular path 930. The first circular path 910, second circular path 920, and third circular path 930 can be determined by annular rings that are rotatably mounted to the gantry 940.

Additionally, alternative embodiments can be used for placing the photon-counting detectors in a predetermined fourth-generation geometry in combination with the detector unit in a predetermined third-generation geometry in the CT scanner.

The detector unit 903 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline, an organic liquid, a plastic, or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs).

The CT scanner also includes a data channel that routes projection measurement results from the photon-counting detectors and the detector unit 903 to a data acquisition system 976, a processor 970, memory 978, network controller 980. The data acquisition system 976 controls the acquisition, digitization, and routing of projection data from the detectors. The data acquisition system 976 also includes radiography control circuitry to control the rotation of the annular rotating frames 910 and 930. In one implementation data acquisition system 976 will also control the movement of the bed 916, the operation of the X-ray source 912, and the operation of the X-ray detectors 903. The data acquisition system 976 can be a centralized system or alternatively it can be a distributed system. In an implementation, the data acquisition system 976 is integrated with the processor 970. The processor 970 performs functions including reconstructing images from the projection data, pre-reconstruction processing of the projection data, and post-reconstruction processing of the image data. The processor 970 also performs the functions and methods described herein.

The pre-reconstruction processing of the projection data can include correcting for detector calibrations, detector nonlinearities, polar effects, noise balancing, and material decomposition. Additionally, the pre-reconstruction processing can include preforming various steps of method 100, including processes 110 and 120.

Post-reconstruction processing can include filtering and smoothing the image, volume rendering processing, and image difference processing as needed. For example, the post-reconstruction processing can be performed using various steps of method 100 (e.g., process 140)

The image-reconstruction process can be performed using filtered back-projection, iterative-image-reconstruction methods, or stochastic-image-reconstruction methods. Additionally, the image-reconstruction processing can include a combined process of reconstructing and denoising the reconstructed images using various steps of method 100 (e.g., process 130).

Both the processor 970 and the data acquisition system 976 can make use of the memory 976 to store, e.g., the projection data 104, reconstructed images, the calibration data 106, various other parameters, and computer programs.

The processor 970 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 978 can be a hard disk drive, CD-ROM drive, DVD drive, FLASH drive, RAM, ROM or any other electronic storage known in the art.

The network controller 980, such as an Intel Ethernet PRO network interface card from Intel Corporation of America, can interface between the various parts of the CT scanner. Additionally, the network controller 980 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus to process projection measurements, the apparatus comprising: processing circuitry configured to obtain projection data comprising recorded counts that (i) correspond to energy bins of a radiation detector, (ii) are affected by pileup of radiation within a detection time window, and (iii) have a pileup-affected spectrum that is distorted relative to a true spectrum of the detected radiation, wherein the recorded counts represent radiation detected at respective photon-counting detector elements comprising the detector, and the detected radiation have been transmitted through an object being imaged, and decompose the projection data into two or more material components by determining final projection lengths of a material decomposition, the final projection lengths being determined by adjusting values of initial projection lengths to optimize a value of an objective function, the objective function comparing the recorded counts of the projection data with calculated counts from a forward model, wherein the forward model receives projection lengths as inputs and outputs pulse pileup-affected counts based on an integral having an integrand comprising a pileup term that is a function of a count rate.

2. The apparatus according to claim 1, wherein the integrand includes both the pileup term and a linear spectral response term.

3. The apparatus according to claim 2, wherein the linear spectral response term comprises another integral having another integrand comprising a detector response function that is independent of pileup effects.

4. The apparatus according to claim 3, wherein the another integrand of the linear spectral response includes an attenuated X-ray spectrum that is attenuated based on multiplying attenuation coefficients of respective material components by the projection lengths of the respective material components, the projection lengths of the respective material components comprising the material decomposition.

5. The apparatus according to claim 1, wherein the pileup term comprises a superposition of products in which respective basis functions are multiplied by corresponding parameterized functions of a count rate.

6. The apparatus according to claim 5, wherein the processing circuitry is further configured to obtain the forward model by obtaining calibration data comprising acquired counts representing the radiation detected at the respective photon-counting detector elements comprising the detector, calculating another objective function that compares acquired counts of the calibration data with the calculated counts of the forward model using given projections lengths, and adjusting parameters of the parameterized functions of the count rate to optimize a value of the another objective function.

7. The apparatus according to claim 5, wherein the parameterized functions of the count rate is a polynomial function with respect to the count rate.

8. The apparatus according to claim 5, wherein the count rate for one of the photon-counting detector elements either is a total count rate corresponding to a sum of count rates of each of the energy bins of the one of the photon-counting detector elements or is a count rate of one of the energy bins of the one of the photon-counting detector elements.

9. The apparatus according to claim 1, wherein the objective function is selected from a Poisson likelihood function, a least-squares difference function, and a weighted least-squares difference function.

10. The apparatus according to claim 1, wherein the material decomposition decomposes an attenuation of radiation incident on one of the photon-counting detector elements into material components each corresponding to respective projection lengths.

11. The apparatus according to claim 1, wherein the processing circuitry is further configured to reconstruct from the final projection lengths computed tomography (CT) images corresponding to respective material components of the material decomposition, and perform image processing on the CT images to reduce noise and/or artifacts.

12. The apparatus according to claim 1, wherein the radiation detector is an X-ray detector and the radiation is X-rays, and the photon-counting detector elements are semiconductor detectors comprising one or more of cadmium telluride (CdTe), cadmium zinc telluride (CZT), silicon (Si), mercuric iodide ($HgI_2$), and gallium arsenide (GaAs).

13. The apparatus according to claim 1, wherein the radiation detector is an X-ray detector and the radiation is X-rays.

14. The apparatus according to claim 1, wherein the photon-counting detector elements are semiconductor detectors comprising one or more of cadmium telluride (CdTe), cadmium zinc telluride (CZT), silicon (Si), mercuric iodide ($HgI_2$), and gallium arsenide (GaAs).

15. A computed tomography (CT) scanner, comprising:
a gantry including a rotating member configured to rotate about an opening configured to accommodate an object being imaged,
a radiation source fixed to the rotating member and configured to radiate radiation towards the opening of the gantry;
a radiation detector comprising a plurality of photon-counting detector elements, the detector configured to detect the radiation transmitted from the ray radiation source after having been transmitted through the opening in the gantry, which is configured to accommodate an object being imaged, the radiation detector generating projection data comprising recorded counts detected at respective photon-counting detector elements comprising the radiation detector, wherein the recorded counts (i) correspond to energy bins of the radiation detector, (ii) are affected by pileup of radiation within a detection time window, and (iii) have a pileup-affected spectrum that is distorted relative to a true spectrum of the detected X rays radiation; and
processing circuitry configured to
obtain a forward model of pulse pileup that calculates counts, which represent the pileup-affected counts, based on projection lengths of a material decomposition, the forward model generating the calculated counts based on an integral having an integrand that comprises a pileup term that is a function of a count rate, and
decompose the projection data into two or more material components by determining final projection lengths of a material decomposition, the final projection lengths being determined by adjusting values of initial projection lengths to optimize a value of an objective function, the objective function comparing the recorded counts of the projection data with calculated counts from the forward model,
wherein the forward model receives projection lengths as inputs and outputs pulse pileup-affected counts based on an integral having an integrand comprising a pileup term that is a function of a count rate.

16. The CT scanner according to claim 15, wherein the radiation detector is an X-ray detector and the radiation is X-rays.

17. An imaging method, comprising:
obtaining projection data comprising recorded counts that (i) correspond to energy bins of a radiation detector, (ii) are affected by pileup of radiation within a detection time window, and (iii) have a pileup-affected spectrum that is distorted relative to a true spectrum of the detected radiation, wherein the recorded counts represent radiation detected at respective photon-counting detector elements comprising the radiation detector, and the detected radiation have been transmitted through an object being imaged; and
decomposing the projection data into two or more material components by determining final projection lengths of a material decomposition, the final projection lengths being determined by adjusting values of initial projection lengths to optimize a value of an objective function, the objective function comparing the recorded counts of the projection data with calculated counts from a forward model,
wherein the forward model receives projection lengths as inputs and outputs pulse pileup-affected counts based on an integral having an integrand comprising a pileup term that is a function of a count rate.

18. The method according to claim 17, further comprising wherein the integrand of the forward model comprises a product multiplying the pileup term by a linear spectral response term, wherein the linear spectral response term includes another integral having another integrand comprising a detector response function that is independent of pileup effects.

19. The method according to claim 17, wherein the pileup term comprises a superposition of products in which respective basis functions are multiplied by corresponding parameterized functions of a count rate.

20. The method according to claim 19, further comprising obtaining calibration data comprising acquired counts representing the radiation detected at the respective photon-counting detector elements comprising the radiation detector, calculating another objective function that compares acquired counts of the calibration data with the calculated counts of the forward model using given projections lengths, and adjusting parameters of the parameterized functions of the count rate to optimize a value of the another objective function.

21. The method according to claim 17, further comprising wherein the count rate for one of the photon-counting detector elements either is a total count rate corresponding to a sum of count rates of each of the energy bins of the one of the photon-counting detector elements or is a count rate of one of the energy bins of the one of the photon-counting detector elements.

22. The method according to claim 17, wherein the step of determining the final projection lengths is performed using the objective function, wherein the objective function is selected from a Poisson likelihood function, a least-squares difference function, and a weighted least-squares difference function.

23. A non-transitory computer-readable medium storing executable instructions, wherein the instructions, when executed by processing circuitry, cause the processing circuitry to perform the method according to claim 17.

24. The method according to claim 17, wherein the radiation detector is an X-ray detector and the radiation is X-rays.

* * * * *